United States Patent [19]

Miyaji et al.

[11] Patent Number: 4,837,344

[45] Date of Patent: Jun. 6, 1989

[54] OPTICALLY ACTIVE BICYCLO CARBOXYLIC ACIDS AND THEIR DERIVATIVES

[75] Inventors: Katsuaki Miyaji; Kazutaka Arai; Yoshio Ohara; Yasuhiro Takahashi, all of Funabashi, Japan

[73] Assignee: Nissan Chemical Industries Ltd., Tokyo, Japan

[21] Appl. No.: 63,076

[22] Filed: Jun. 17, 1987

[30] Foreign Application Priority Data

Jun. 19, 1986 [JP] Japan .................................. 61-143447
Aug. 8, 1986 [JP] Japan .................................. 61-187050

[51] Int. Cl.4 ............................................ C07D 307/20
[52] U.S. Cl. ...................................... 549/319; 549/318
[58] Field of Search .................................. 549/318, 319

[56] References Cited

U.S. PATENT DOCUMENTS 4,007,211  2/1977  Trost et al. .
4,122,093  10/1978  Corey et al. .
4,126,622  11/1978  Tomoskozi et al. .

FOREIGN PATENT DOCUMENTS 173142  3/1986  European Pat. Off. ............ 549/318

OTHER PUBLICATIONS

J. of the Am. Chem. Soc., 97, No. 23, 11/12/75, pp. 6908-6909; E. J. Corey, I et al.: "Preparation of an optically active prostaglandin intermediate via asymmetric induction" *p. 6908, formula 3*.

Tetrahedron Letters, vol. 26, No. 26, 1985, pp. 3095-3098, GB; T. Poll, et al. "Diastereoface-discriminative metal coordination in asymmetric synthesis: D-pantolactone as practical chiral auxiliary for Lewis acid catalyzed Diels-Alder reactions", p. 3096, last 2 parag., p. 3097, reaction scheme .

J. of the Am. Chem. Soc., 99, No. 9, 4/27/77, pp. 3101-3113, US; B. M. Trost, et al.: "New synthetic reactions. Oxidative decarboxylation of alpha-methylthiocarboxylic acids, new approach to acyl anion and ketene synthons" * p. 3109, para. Prep. of 7-anti-Methoxymethylbicyclo . . .

J. of the Am. Chem. Soc., vol. 97, No. 12 6/12/75, pp. 3528-3530; B. M. Trost, et al.: "New synthetic reactions. Oxidative decarboxylation". *p. 3529, right-hand column, reaction scheme leading to compound No. 8*.

Chem. Abstracts, 97, No. 13, 9/27/82, p. 574, abstr. No. 109695e, Columbus, OH US; & SU-A-906,987 (I. M. Akhmedov, et al.) Feb. 2, 1982.

Chem. Abstracts, 87, No. 1 Jul. 4, 1977, p. 443, abstr.

No. 5513a, Columbus, OH, US; & JP-A-77 14759 (Hitachi Chemical Co., Ltd.) Feb. 3, 1977.

J. of Organic Chemistry, 50, No. 12, 1985, pp. 2115-2121; H. W. Thompson, et al.: "Synthesis of 2,2-Disubstituted 7-Methylenenorbornanes with 2-exo functionality by Diels-Alder reaction of 5,5-dimethoxytetrachlorocyclopent adicen" p. 2115, abstr; p. 2117, scheme I*.

J. of the Am. Chem. Soc., 93, No. 6 Mar. 6, 1971, pp. 1491-1493; E. J. Corey, II et al.: "New reagents for stereoselectie carbonyl reduction. An improved synthetic route to the primary prostaglandins".

Primary Examiner—Glennon H. Hollrah
Assistant Examiner—Patricia L. Morris
Attorney, Agent, or Firm—Oblon, Fisher, Spivak, McClelland & Maier

[57] ABSTRACT

A compound having the formula:

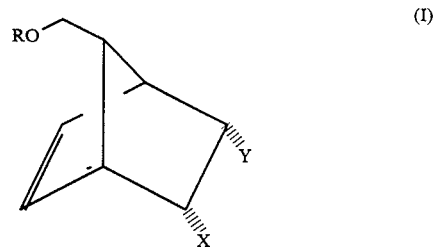

(I)

wherein R is a hydroxyl-protecting group, X is a hydrogen atom, $CO_2R'$ (wherein R' is a hydrogen atom or an alkyl group having from 1 to 7 carbon atoms, or $CO_2R'$ is a salt of $CO_2H$), or a group of the formula:

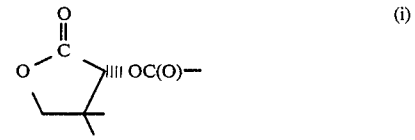

(i)

and when X is a hydrogen atom, Y is $CO_2R'$ (wherein R' is as defined above) or a group of the formula:

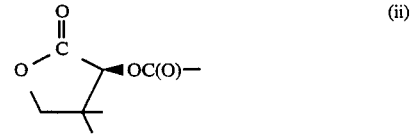

(ii)

and when X is $CO_2R'$ or the group of the formula (i), Y is a hydrogen atom.

5 Claims, No Drawings

OPTICALLY ACTIVE BICYCLO CARBOXYLIC ACIDS AND THEIR DERIVATIVES

The present invention relates to a novel intermediate for Corey lactone and its optical antipode as an intermediate for prostaglandins useful as pharmaceutical, and to a process for its preparation. The novel intermediate is represented by the formula:

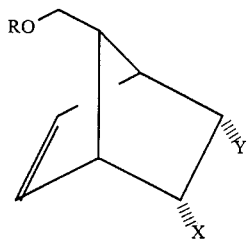
(I)

wherein R is a hydroxyl protecting group, X is a hydrogen atom, $CO_2R'$ (wherein R' is a hydrogen atom or an alkyl group having from 1 to 7 carbon atoms, or $CO_2R'$ is a salt of $CO_2H$), or a group of the formula:

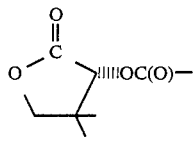
(i)

and when X is a hydrogen atom, Y is $CO_2R'$ (wherein R' is as defined above) or a group of the formula:

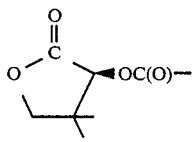
(ii)

and when X is $CO_2R'$ or the group of the formula (i), Y is a hydrogen atom.

Prostaglandins are physiologically active substances and play an essential role for the maintenance of the normal function of living bodies. Thus, they are expected to be used as medicines in various fields. Some of them have been practically used in the fields of induction of labor and improvement of the peripheral blood flow.

Among chemical syntheses of prostaglandins, the most effective one is a method reported by Corey et al wherein Corey lactone of the formula:

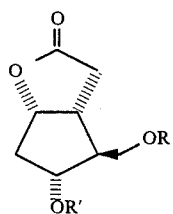
(IV)

wherein each of R and R' is a hydrogen atom or a hydroxyl-protecting group is used as a key intermediate (references: JACS 92 397 (1970), JACS 93 1490 (1971)). Corey lactone is an indispensable compound for the synthesis of prostaglandins since many prostaglandins are presently prepared via Corey lactone.

The compound represented by the above formula (I) is an important intermediate for the preparation of an optical isomer of this Corey lactone. A number of methods are known for the preparation of optically active Corey lactone. Among them, the following four methods are regarded as being excellent.

(1) Corey method: Synthesis wherein the Diels-Alder reaction of a cyclopentadiene derivative and the optical resolution of a hydroxy carboxylic acid are key steps (references: JACS 92 397 (1970), JACS 93 1489 (1971))

(2) Chinoin method: Synthesis wherein the Prins reaction of an optically active bicyclic lactone obtained by optical resolution is a key step (references: Japanese Unexamined Patent Publication No. 105163/1977, TL 4639 (1976))

(3) Pfizer method: Synthesis in which the Prins reaction of norbornadiene and optical resolution of carboxylic acid are key steps (references: Japanese Unexamined Patent Publication No. 111074/1975, JACS 95 7522 (1973))

(4) Asymmetric Diels-Alder method: Synthesis in which the asymmetric Diels-Alder reaction using (−)-Pregone as the asymmetric source is a key step (reference: JACS 97 6908 (1975))

Each of the above three methods (1) to (3) involves optical resolution, and thus requires an expensive agent for optical resolution and involves a cumbersome operation for the optical resolution. Besides, there is a problem such that the enantiomer which is not required, will be wasted. Whereas, the asymmetric Diels-Alder method (4) is an excellent method whereby Corey lactone can be produced in good yield with high selectivity without optical resolution. However, the conventional asymmetric Diels-Alder method carried out by Corey et al requires, as the asymmetric source, (−)-Pregone which is hardly available on a commercial scale and which is hardly synthesised in high optical purity (references: Angew. Chem. 73 240 (1961)), JOC 41 380 (1976), T. L. 514 (1977)) Thus, this method is not suitable for an industrial process.

For the above-mentioned reasons, it has been desired to develop a process for preparing optically active Corey lactone by an asymmetric Diels-Alder method by using a more readily available asymmetric source.

The present inventors have extensively studied asymmetric sources readily available on an industrial scale, and as a result, have found that by utilizing optically active pantolactone, the asymmetric Diels-Alder reaction proceeds in good yield with high steric selectivity in the presence of a Lewis acid, whereby the above problems can be solved.

Heretofore, an asymmetric Diels-Alder reaction of an unsubstituted cyclopentadiene with an acrylic acid ester of optically active pantolactone having the following formula (II)-1 or (II)-2 (reference: Poll Thomas et al., T. L. 26 3095 (1985) has been known. The present inventors have applied this reaction to a 5-mono-substituted cyclopentadiene of the formula III instead of the unsubstituted cyclopentadiene, within a temperature range from −100° to 0° C., preferably from −65° to −40° C.

The present inventors have found that the reaction can be conducted in good yield with high steric selectivity, inspite of the fact that the compound of the formula (III) is very susceptible to isomerization, and the asymmetric Diels-Alder reaction is usually likely to be led to a reduction in the yield or deterioration in the selectivity even with a slight change in the substrate.

The present inventors have found that when a compound having the following formula (II)-1 or (II)-2:

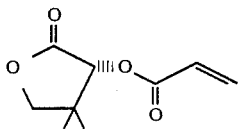
(II)-1

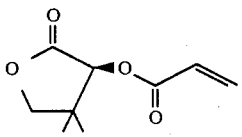
(II)-2 and a 5-mono-substituted cyclopentadiene having the formula:

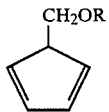
(III)

wherein R is a hydroxyl-protecting group are reacted in the presence of a Lewis acid, an optically active pantolactone ester of bicyclo[2.2.1]hept-5-ene-2-endo-carboxylic acid [a compound of the following formula (I)—(X=lactone) as derived from the starting material of the formula (II)-1, or a compound of the following formula (I)—(Y=lactone) as derived from the starting material of the formula (II)-2]:

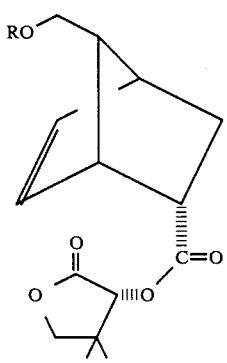
(I)-(X = lactone)

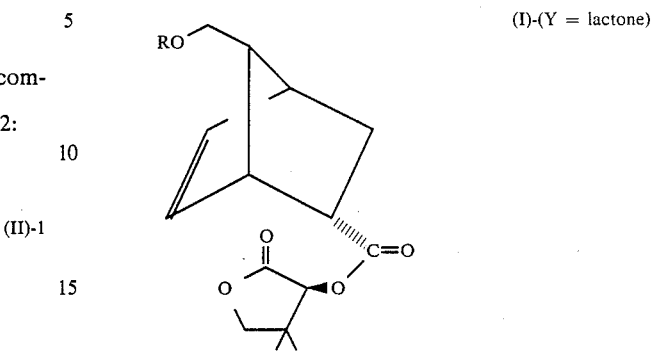
(I)-(Y = lactone)

can be obtained in good yield with high selectivity.

Free carboxylic acids of the formulas (I)—(X=$CO_2H$) and (I)—(Y=$CO_2H$) obtained by the hydrolysis of the optically active compounds of the formulas (I)—(X=lactone) and (I)—(Y=lactone) are both new compounds. These lactones have a high level of crystallinity, and accordingly they can readily be purified chemically and optically. This is one of the features in which the present process is superior to the conventional methods.

Further, these carboxylic acids of the formulas (I)—(X=$CO_2H$) and (I)—(Y=$CO_2H$) can be converted to the corresponding alkyl esters of the formulas (I)—(X=ester) and (I)—(Y=ester) by a usual method, e.g. by subjecting them to diazomethane treatment, or by converting them to their acid chlorides, followed by the reaction with an alcohol in the presence of an agent for removing hydrochloric acid.

As shown in the following illustration and Reference Examples, the compounds of the formulas (I)—(X=lactone), (I)—(X=ester) and (I)—(X=$CO_2H$) can be converted to an optically active ketone of the formula (V) by a Corey method (reference: JACS 97 6908 (1975)) or a Trost method (reference: JACS 97 3528 (1975)), respectively, and then converted to optically active Corey lactone in good yield by a Corey method. Likewise, by using compounds of the formulas (I)—(Y=lactone), (I)—(Y=ester) and (I)—(Y=$CO_2H$), optical antidotes of the compounds of the formulas (V), (VI) and (IV) can be obtained.

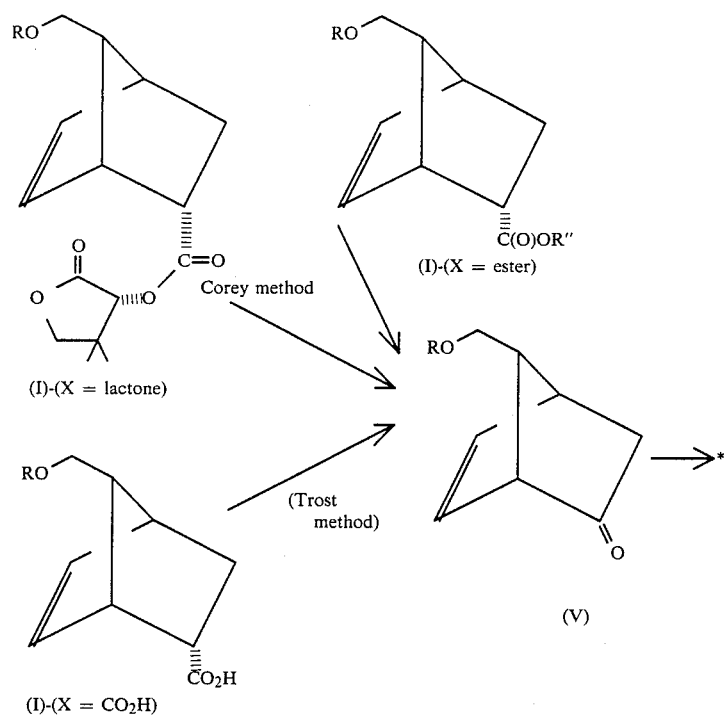
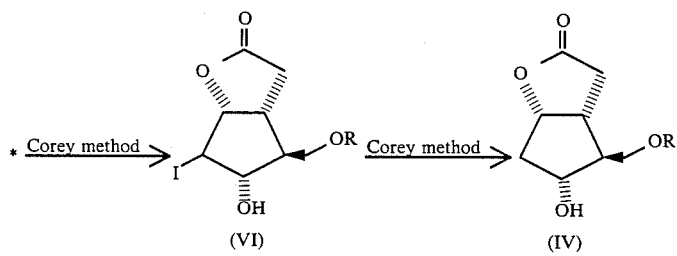
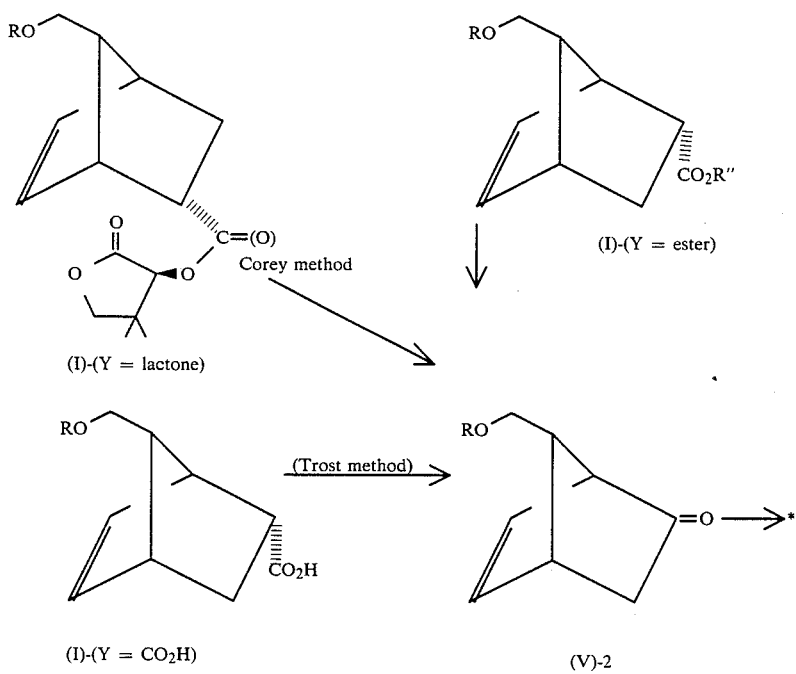

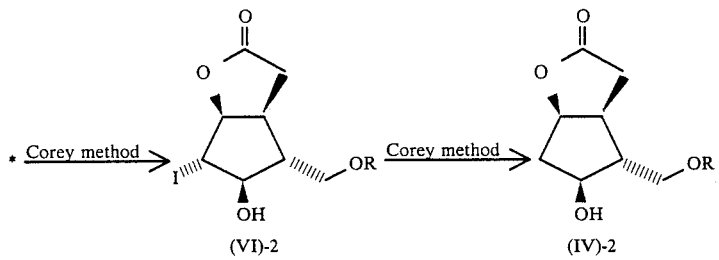

In the above formulas, R″ is an alkyl group having from 1 to 7 carbon atoms.

From the foregoing, an industrially advantageous process for preparing optically active Corey lactone by an asymmetric Diels-Alder method by using an industrially readily available asymmetric source, has been established.

Now, the present invention will be described in detail with reference to the preferred embodiments.

The optically active acrylic acid ester of pantolactone of the formula (II)-1 or (II)-2 is reacted with a Lewis acid at a low temperature in an organic solvent.

The organic solvent to be used here includes an aromatic solvent such as benzene, toluene, xylene or chlorobenzene and a halogenated alkane solvent such as dichloromethane, chloroform or carbon tetrachloride. Further, a solvent mixture of these solvents and a solvent mixture with a paraffin solvent such as petroleum ether or n-hexane, may be mentioned.

The Lewis acid to be used includes $SnCl_4$, $TiCl_4$, $AlCl_3$ and $EtAlCl_2$. The Lewis acid is used in an amount of from 0.1 to 3 mol, preferably from 0.3 to 1 mol, per mol of the starting material ester.

The reaction temperature is usually within a range of from −70° to 20° C., preferably from −35° to 0° C.

The reaction system is further cooled to a lower temperature, and the 5-mono-substituted cyclopentadiene of the formula (III) is added thereto by itself or in the form of a solution in the above-mentioned solvent. Then, the reaction is conducted at a low temperature, whereby an optically active bicyclo[2.2.1]hept-5-ene-2-endocarboxylic acid pantolactone ester is obtained as a compound of the formula (I)—(X=lactone) or (I)—(Y=lactone).

The 5-mono-substituted cyclopentadiene is added in an amount of from 0.5 to 10 mol, preferably from 1 to 3 mol, per mol of the starting material acrylic acid ester.

The hydroxyl-protecting group for R in the general formula, is stable one against a Lewis acid at a low temperature and yet stable one also against alkaline substance. Such a protecting group includes a benzyl group, a benzyl group substituted on the benzene ring by one or two bromine atoms, chlorine atoms or lower alkyl groups; a lower alkoxy methyl group represented by an example of a methoxymethyl group; and a lower alkylated silyl group such as a t-butyldiphenylsilyl group or a t-butyldimethylsilyl group.

The reaction temperature is usually within a range of from −100° to 0° C., preferably from −65° to −40° C. The reaction time is usually within a range of from 1 to 48 hours, preferably from 5 to 20 hours.

The Diels-Alder adduct obtained by the asymmetric Diels-Alder reaction of the present invention was analyzed by HPLC, whereby the ratio of the desired product of the formula (I)—(X=lactone) or (I)—(Y=lactone) to its diastereomer was found to be very high at a level of "97:3 or less".

The desired product is highly crystallizable, and can readily be chemically and optically purified by recrystallization.

The optically active ester of the formula (I)—(X=lactone) or (I)—(Y=lactone) can be converted to an optically active carboxylic acid of the formula (I)—(X=$CO_2H$) or (I)—(Y=$CO_2H$), respectively, by hydrolyzing it under such a condition that no removal of the hydroxyl-protecting group or no epimerization takes place. As the hydrolytic condition, it is preferred to employ an alkaline hydrolysis by means of an alkali metal hydroxide such as sodium hydroxide, lithium hydroxide or potassium hydroxide.

This hydrolysis brings about no epimerization or racemization, and it is possible to readily obtain chemically and optically pure, optically active carboxylic acid.

The carboxylic acid of the formula (I)—(X=$CO_2H$) or (I)—(Y=$CO_2H$) can be converted to its methyl ester by treating it with diazomethane in an innert solvent such as ethyl ether. Otherwise, it may be first converted to its acid chloride by a chlorination agent such as thionyl chloride and then esterified with an alcohol having from 1 to 7 carbon atoms in the presence of an agent for removing hydrochloric acid such as pyridine to obtain an ester of the formula (I)—(X=ester) or (I)—(Y=ester). Further, such esterification can be conducted also by a usual esterification in the absence of an acidic catalyst.

According to the process of the present invention, an optically active novel ester such as a compound of the formula (I)—(X=lactone), (I)—(X=ester), (I)—(Y=lactone) or (I)—(Y=ester) and an optically active novel carboxylic acid such as a compound of the formula (I)—(X=$CO_2H$) or (I)—(Y=$CO_2H$) can be produced in good yield with high selectivity by using a readily available asymmetric source (D- or L-pantolactone). Racemic modifications of the compounds of the formulas (I)—(X=ester), (I)—(Y—ester), (I)—(X=$CO_2H$) and (I)—(Y=$CO_2H$) are known (references: U.S. Pat. No. 4,007,211, JACS., 97 (12) 3528, JACS., 99, (9) 3101). However, for the production of optically active Corey lactones and prostaglandins from such racemic modifications, a cumbersome and inefficient operation for optical resolution has been required. As a result of the present invention, it has now been made very easy to produce optically active Corey lactones and prostaglandins on an industrial scale.

Now, the present invention will be described in further detail with reference to Examples and Reference Examples. However, it should be understood that the present invention is by no means restricted by these specific Examples.

EXAMPLE 1

2.4 g (13.0 mmol) of an acrylic acid ester of D-pantolactone (compound of the formula (II)-1) was dissolved in 24 ml of a solvent (dichloromethane/petroleum ether=7/1 (v/v)), and the solution was cooled to −15° C. To this solution, 6.5 ml of a 1M solution of titanium tetrachloride in peteroleum ether was dropwise added. The mixture was stirred at this temperature for 30 minutes, and then cooled to −60° C. Then, 5.93 g (31.9 mmol) of 5-benzyloxymethylcyclopentadiene (compound of the formula (III), R=CH₂Ph) was added thereto, and the mixture was stirred at −60° C. for 10 hours. The temperature was raised to 0° C. over a period of 13 hours, and then 13.4 g of sodium carbonate decahydrate was added. The mixture was stirred at room temperature for 30 minutes. Formed precipitates were separated by filtration, and the solvent was distilled off. The oily substance thus obtained was purified by silica gel column chromatography (200 g, eluted with hexane/ethyl ether=2/1 (v/v)) to obtain 3.56 g (yield: 74%) of brown crystals. The crystals were analyzed by HPLC (YMC-PACK A-303 ODS, methanol/water=4/1 (v/v)), whereby the ratio of the desired compound 2S-bicyclo[2.2.1.]hept-5-ene-2-endo-carboxylic acid D-pantolactone ester [(I)—(X=lactone), R=CH₂Ph] to its diastereomer was found to be 98 to 2. The brown crystals were recrystallized from hexane/ethyl ether to obtain the desired compound as pure white crystals.

$^1$H-NMR (400 MHz, CDCl$_3$) δ(ppm):
1.13(3H, s), 1.17(3H, s), 1.52(1H, dd, J=12 Hz, J=4 Hz),
2.03(1H, ddd, J=12 Hz, J=9 Hz, J=4 Hz), 2.15(1H, t, J=7 Hz),
2.86(1H, br t), 3.19(1H, dt, J=9 Hz, J=4 Hz), 3,24(1H, m),
3.36(2H, dd, J=7 Hz, J=3 Hz), 4.00(1H, d, J=9 Hz), 4.05(1H, d, J=9 Hz), 4.44(2H, s), 5.31(1H, s),
5.79(1H, dd, J=6 Hz, J=3 Hz), 6.13(1H, dd, J=6 Hz, J=3 Hz),
7.2–7.4(5H, m)
MS: M+ =370, [M—PhCH₂]+ =279
[M-185]+ =185 (Retro Diels-Alder reaction)
m.p.: 96.0°–96.5° C.
$[\alpha]_D^{25}$ = −57.8° (c=1.00, MeOH)

The diastereomer ratio was determined in the following manner.

A racemic modification of an acrylic ester of pantolactone (mixture of (II)-1/(II)-2 = 1/1) prepared from DL-pantolactone and acrylic acid, was treated under the same reaction conditions as described above to obtain two types of diastereomers (mixture of (I)—(X=lactone) and (I)—(Y=lactone)) in a yield of 77%. This mixture was analyzed by HPLC, whereby two peaks attributable to the respective diastereomers were separated 1:1. The diastereomer ratios of Examples 1 and 8 were determined by the area ratio of these two peaks.

EXAMPLE 2

1.56 g (4.22 mmol) of 2S-bicyclo[2.2.1]hept-5-ene-2-endo-carboxylic acid D-pantolactone ester [(I)—(X=lactone), (R=CH₂Ph] prepared in Example 1, was dissolved in 20 ml of a solvent (water/THF=1/1 (v/v)), and 0.43 g (17.9 mmol) of lithium hydroxide was added. The mixture was stirred at room temperature for 24 hours. After distilling off THF, the mixture was acidified by an addition of 6 ml of 10% hydrochloric acid, and extracted three times with 15 ml of a solution (n-pentane/dichloromethane=98/2 (v/v)). The organic layer was dried with magnesium sulfate. Then, the solvent was distilled off to obtain 1.08 g (yield 99%) of oily desired product 2S-bicyclo[2.2.1]hept-5-ene-2-endo-carboxylic acid [(I)—(X=CO₂H), R=CH₂Ph]. When cooled in a refrigerator, this product solidified to form white crystals.

$^1$H-NMR (90 MHz, CDCl$_3$) δ(ppm):
1.36(1H, dd), 1.91(1H, dd), 2.07(1H, t),
2.81(1H, m), 3.00(1H, dt), 3.17(1H, m),
3.34(2H, d), 4.4(2H, s), 5.86(1H, dd),
6.04(1H, dd), 7.2–7.6(5H, m)
MS: M+ =258, [M—CH₂Ph]+ =167
[CH₂Ph]+ =91, [M-179] (Retro Diels-Alder reaction)
m.p.: 40.5°–41.5° C.
$[\alpha]_D^{25}$ = −49.3° (c=1.005, MeOH)

EXAMPLE 3

Synthesis of 7-anti-benzyloxymethylbicyclo[2.2.1]-hept-5-ene-2S-endocarboxylic acid methyl ester 144 mg of 2S-bicyclo[2.2.1]hept-5-ene-2-endo-carboxylic acid [(I)—(X=CO₂H), R=CH₂Ph] was dissolved in 5 ml of diethyl ether. Then, diazomethane was blown into this and saturated, and the solution was left to stand for one hour. Then, nitrogen was blown into the solution, and after removing excess diazomethane, the solvent was distilled off. The residue was purified by silica gel column chromatography (7 g eluted with hexane/ethyl ether=2/1) to obtain 125 mg (yield: 82%) of an oily methyl ester [compound of the formula (I)—(X=ester), R=CH₂Ph, R"=Me].

$^1$H-NMR (60 MHz, CDCl$_3$)
δ(ppm); 1.43(1H, dd, J=11 Hz, J=4 Hz), 1.73–2.3(2H, m),
2.7–3.2(3H, m), 3.3(2H, d, J=7 Hz), 3.53(3H, s), 4.35(2H, s), 5.74(1H, dd, J=7 Hz, J=2 Hz), 5.98(1H, dd, J=7 Hz, J=2 Hz),
7.3(5H, br s)
IR: 1730(cm$^{-1}$), 740, 720, 700
MS: M+ =272, [M—CH₂Ph]+ =181,
[CH₂Ph]+ =91
$[\alpha]_D^{25}$ = −48.3° (c=0.933, MeOH)

EXAMPLE 4

Synthesis of 7-anti-benzyloxymethylbicyclo[2.2.1]-hept-5-ene-2S-endo-carboxylic acid ethyl ester 50 mg of 2S-bicyclo[2.2.1]hept-5-ene-2-endo-carboxylic acid [(I)—(X=CO₂H), R=CH₂Ph] was dissolved in 4 ml of carbon tetrachloride. Then, 0.38 ml of thionyl chloride was added thereto, and the mixture was refluxed under heating for 3 hours. The solvent and excess thionyl chloride were distilled off under reduced pressure, and then, 2 ml of dried toluene, 0.02 ml of dried pyridine and 0.02 ml of dried ethanol were added. The mixture was stirred at room temperature for 4 hours. It was washed with 10% hydrochloric acid and then with a saturated sodium hydrogen carbonate aqueous solution. Then, the organic layer was dried over magnesium sulfate. The solvent was distilled off, and the residue was purified by silica gel column chromatography (4 g, eluted with hexane/ethyl ether=2/1 (v/v)) to obtain 37 mg (yield 67%) of an oily ethyl ester [(I)—(X=ester), R=CH₂Ph, R"=Et].

$^1$H-NMR (60 MHz, CDCl$_3$)
δ(ppm; 1.2(3H, t, J=9 Hz), 1.3–2.3(3H, m), 2.7–3.3(3H, m), 3.33(2H, d, J=7 Hz), 4.05(2H, q, J=9 Hz),
4.38(2H, s), 5.79(1H, dd, J=7 Hz, J=2 Hz),
6.07(1H, dd, J=7 Hz, J=2 Hz), 7.3(5H, br s)
IR: 1730 (cm$^{-1}$), 740, 720, 700
MS: M$^+$=286, [M—CH$_2$Ph]$^+$=195
[CH$_2$Ph]$^+$=91
$[\alpha]_D^{25}$=−55° (c=0.369, MeOH)

EXAMPLE 5

Synthesis of 7-anti-benzyloxymethylbicyclo[2.2.1]-hept-5-ene-2S-endo-carboxylic acid isoamyl ester 0.30 g of 2S-bicyclo[2.2.1]hept-5-ene-2-endo-carboxylic acid [(I)—(X=CO$_2$H), R=CH$_2$Ph] was dissolved in 6 ml of carbon tetrachloride. Then, 1 ml of thionyl chloride was added thereto, and the mixture was refluxed under heating for 3 hours. The solvent and excess thionyl chloride were distilled off under reduced pressure, and 5 ml of dried toluene, 0.11 ml of dried pyridine and 0.40 ml of dried isoamyl alcohol were added thereto. The mixture was stirred for 16 hours at room temperature. After an addition of 50 ml of ethyl ether, the reaction solution was washed with 10% hydrochloric acid and then with a saturated sodium hydrogen carbonate aqueous solution, and dried over magnesium sulfate. The solvent was distilled off, and the residue obtained was purified by silica gel column chromatography (20 g, eluted with hexane/ethyl ether=3/1 (v/v)) to obtain 0.30 g (yield: 79%) of an oily isoamyl ester [(I)—(X=ester), R=CH$_2$Ph, R″=isoamyl].
$^1$NMR (60 MHz, CDCl$_3$)
δ(ppm); 0.90(6H, d, J=6 Hz), 1.1–2.3(6H, m),
2.7–3.2(3H, m), 3.3(2H, d, J=7 Hz), 4.0(2H, t, J=7 Hz),
4.34(2H, s), 5.72(1H, dd, J=6 Hz, J=2 Hz),
5.98(1H, dd, J=6 Hz, J=2 Hz), 7.4(5H, br s)
IR: 1730 (cm$^{-1}$), 740, 720, 700
MS: M$^+$=328
$[\alpha]_D^{25}$=−56.5° (c=1.045, MeOH)

EXAMPLE 6

Synthesis of 7-anti-benzyloxymethylbicyclo[2.2.1]-hept-5-ene-2S-endo-carboxylic acid s-hexyl ester 0.30 g of 2S-bicyclo[2.2.1]hept-5-ene-2-endo-carboxylic acid [(I)—(X—CO$_2$H), R=CH$_2$Ph] was dissolved in 6 ml of carbon tetrachloride. Then, 1 ml of thionyl chloride was added thereto, and the mixture was refluxed under heating for 3 hours. The solvent and excess thionyl chloride was distilled off under reduced pressure, and 5 ml of dried toluene, 0.11 ml of dried poyridine, 0.40 ml of dried s-hexyl alcohol were added. The mixture was stirred for 20 hours at room temperature. After an addition of 50 ml of ethyl ether, the reaction solution was washed with 10% hydrochloric acid and then with a saturated sodium hydrogen carbonate aqueous solution, and dried over magnesium sulfate. The solvent was distilled off, and the residue obtained was purified by silica gel column chromatography (20 g, eluted with hexane/ethyl ether=3/1 (v/v)) to obtain 0.21 g (yield: 53%) of an oily s-hexyl ester [(I)—(X=ester), R=CH$_2$Ph, R″=CH(CH$_3$)(CH$_2$)$_3$CH$_3$].
$^1$H-NMR (60 MHz, CDCl$_3$)
δ(ppm); 0.6–1.7(10H, m), 1.7–2.3(4H, m),
2.7–2.9(4H, m), 3.2(2H, d, J-7 Hz), 4.3(2H, s),
4.8(1H, br q), 5.7(1H, dd, J=6 Hz, J=3Hz),
6.0(1H, dd, J=6 Hz, J=3 Hz), 7.0–7.5(5H, m)
IR: 1720 (cm$^{-1}$), 740, 720, 700
MS: M$^+$=342
$[\alpha]_D^{25}$=−54.6° (c=1.024, MeOH)

EXAMPLE 7

Synthesis of 7-anti-benzyloxymethylbicyclo[2.2.1]-hept-5-ene-2S-endo-carboxylic acid D-pantolactone ester 0.51 g of 2S-bicyclo[2.2.1]hept-5-ene-2-endo-carboxylic acid [(I)—(X=CO$_2$H), R=CH$_2$Ph] was dissolved in 6 ml of carbon tetrachloride. Then, 0.6 ml of thionyl chloride was added thereto, and the mixture was refluxed under heating for 3 hours. The solvent and excess thionyl chloride were distilled off under reduced pressure, and then 6 ml of dried toluene, 0.18 ml of dried pyridine and 0.28 g of D-pantolactone were added thereto. The mixture was stirred at room temperature for 3 hours. The organic layer was washed with 10% hydrochloric acid and then with a saturated sodium hydrogen carbonate aqueous solution, and dried over magnesium sulfate. The solvent was distilled off, and the residue obtained was purified by silica gel column chromatography (10 g, eluted with hexane/ethyl ether=2/1 (v/v)) to obtain 0.66 g (yield: 90%) of a D-pantolactone ester [(I)—(X=lactone), R=CH$_2$Ph].
$^1$H-NMR (90 MHz, CDCl$_3$)
δ(ppm); 1.13(3H, s), 1.17(3H, s), 1.52(1H, d, J=12 Hz),
2.00(1H, dd, J=12 Hz, J=9 Hz), 2.15(1H, t, J=7 Hz),
2.86(1H, br t), 3.0–3.3(2H, m), 3.36(2H, d, J=7 Hz),
4.00(1H, s), 4.44(2H, s), 5.31(1H, s),
5.79(1H, dd, J=6 Hz, J=3 Hz),
6.13(1H, dd, J=6 Hz, J=3 Hz), 7.2–7.4(5H, m)
IR: 1790 (cm$^{-1}$), 1730, 740, 720, 700
MS: M$^+$=370, [M—CH$_2$Ph]$^+$=279,
[M=185]$^+$=185 (Retro Diels-Alder reaction)
mp: 96.0°–96.5° C.
$[\alpha]_D^{25}$=−57.8° (c=1.00, MeOH)

EXAMPLE 8

2.4 g (13.0 mmol) of an acrylic acid ester of L-pantolactone (compound of the formula (II)-2) was dissolved in 24 ml of a solvent (dichloromethane/petroleum ether=7/1 (v/v)), and the solution was cooled to −15° C. To this solution, 6.5 ml of a 1M solution of titanium tetrachloride in petroleum was dropwise added. The mixture was stirred at this temperature for 30 minutes, and then cooled to −60° C. Then, 5.93 g (31.9 mmol) of 5-benzyloxymethylcyclopentadiene [compound of the formula (III), R=CH$_2$Ph] was added thereto, and the mixture was stirred at −60° C. for 10 hours. Then, the temperature was raised to 0° C. over a period of 13 hours, and then 13.4 g of sodium carbonate decahydrate was added thereto. The mixture was stirred at room temperature for 30 minutes. Formed precipitates were separated by filtration, and then the solvent was distilled off. The oily substance thus obtained was purified by silica gel column chromatography (200 g, eluted with hexane/ethyl ether=2/1 (v/v)) to obtain 3.56 g (yield: 74%) of brown crystals. The crystals were analyzed by HPLC (YMC-PACK A-303 ODS, methanol/water=4/1 (v/v)), whereby the ratio of desired compound 2R-bicyclo[2.2.1]hept-5-ene-2-endo-carboxylic acid L-pantolactone ester [(I)—(Y=lactone), R=CH$_2$Ph] to its diastereomer was found to be "98 to 2". The brown crystals were recrystallized from a hexane/ethyl ether solution to obtain the desired compound as pure white crystals.
$^1$H-NMR (400 MHz, CDCl$_3$) δ(ppm);
1.13(3H, s), 1.17(3H, s), 1.52(1H, dd, J=12 Hz, J=4 Hz), 2.03(1H, ddd, J=12 Hz, J=9 Hz, J=4 Hz),
2.15(1H, t, J=7 Hz), 2.86(1H, br t),
3.19(1H, dt, J=9 Hz, J=4 Hz), 3.24(1H, m),
3.36(2H, dd, J=7 Hz, J=3 Hz), 4.00(1H, d, J=9 Hz),
4.05(1H, d, J=9 Hz), 4.44(2H s), 5.31(1H, s)
5.79(1H, dd, J=6 Hz, J=3 Hz), 6.13(1H, dd, J=6 Hz, J=3 Hz),
7.2–7.4(5H, m)
MS; M+ =370, [M—PhCH$_2$]+ =279,
[M-185]+ =185 (Retro Diels-Alder reaction)
m.p. 96.0°–96.5° C.
$[\alpha]_D^{25}$= +57.8° (c=1.00, MeOH)

Now, as an example for leading to Corey lactone, 2S-bicyclo[2.2.1]hept-5-ene-2-endo-carboxylic acid [(I)—(X=CO$_2$H), R=CH$_2$Ph] was converted to an optically active ketone of the formula (V) by the method of Trost et al (reference: JACS 97 3528 (1975)) (see Reference Example 1), and further the ketone of the formula (V) was converted to an optically active iodo lactone of the formula (VI) by the method of Corey et al. (reference: JACS 97 6908 (1975)) (see Reference Example 2), and the results will be given below.

Reference Example 1

15 ml (10.7 mmol) of dissopropylamine was dissolved in 17 ml of dried THF, and the solution was cooled to −78° C. under an argon atmosphere. To this solution, 6.4 ml (10.0 mmol) of a hexane solution of 1.57M n-butyllithium was dropwise added. The mixture was stirred at 0° C. for one hour, and then cooled to −30° C. To this mixture, a solution prepared by dissolving 1.08 g (4.19 mmol) of 2S-bicyclo[2.2.1]hept-5-ene-2-endo-carboxylic acid [(I)—(X=CO$_2$H), R=CH$_2$Ph] and 0.88 ml (5.06 mmol) of HMPA in 5 ml of dried tetrahydrofuran, was dropwise added, and the mixture was stirred at 0° C. for 3 hours. Then, the mixture was cooled to −10° C., and 0.56 ml (6.21 mmol) of dimethyldisulfide was added thereto. The mixture was stirred at 0° C. for 2 hours. The reaction solution was poured into ice water, and extracted with ethyl ether. The aqueous layer was acidified with 1N hydrochloric acid, then saturated with sodium chloride, and extracted with ethyl ether. The organic layers were put together, and the solvent was distilled off to obtain an oily substance. The oily substance was dissolved in 10 ml of dried ethanol, and 0.86 g of sodium carbonate and 0.96 g (7.19 mmol) of N-chlorosuccinimide were added thereto at 0° C. The mixture was stirred under an argon atmosphere at room temperature for 3 hours. Then, 0.7 ml of a saturated sodium sulfite aqueous solution, 12 ml of 1N hydrochloric acid and 3 ml of ethyl ether were added thereto, and the mixture was stirred at room temperature for further 5 hours. The reaction solution was poured into ice water, saturated with sodium chloride, and extracted three times with ethyl ether and twice with dichloromethane. The organic layers were put together and dried over magnesium sulfate. Then, the solvent was distilled off. The oily substance thus obtained was purified by silica gel column chromatography (60 g, eluted with hexane/ethyl ether=2:1 (v/v)) to obtain 0.49 g (yield: 51%) of an optically active ketone of the formula (V).
$^1$H-NMR (90 MHz, CDCl$_3$)
1.98(2H, t), 2.72(1H, t), 3.00(1H, m), 3.14(1H, m),
3.52(2H, d), 4.46(2H, s), 5.92(1H, dd), 6.40(1H, dd),
7.3(5H, m)
$[\alpha]_D^{25}$= −420° (c=0.376, CHCl$_3$)

Reference Example 2

To 5 ml of dried dichloromethane, 220 mg (0.89 mmol) of m-chloroperbenzoic acid having a purity of 70% and 12.0 mg (1.13 mmol) of sodium carbonate were added. Then, 160 mg (0.70 mmol) of the ketone of the formula (V) dissolved in 3 ml of dried dichloromethane was added under cooling with ice, and the mixture was stirred at 0° C. for 4 hours. Then, 6 ml of a saturated sodium sulfite aqueous solution was added thereto, and the mixture was stirred for a while, and then extracted with dichloromethane. The organic layer was washed with an aqueous sodium sulfite solution, and dried over magnesium sulfate. Then, the solvent was distilled off to obtain 165 mg of oily lactone. Then, 3 ml of methanol and 2 ml of water were added thereto, and then 83 mg (2.1 mmol) of sodium hydroxide was added. The mixture was stirred at room temperature for 3 hours. Methanol was distilled off under reduced pressure and the aqueous layer was neutralized with carbondioxide. Then, 0.52 g of iodine and 1.02 g of potassium iodide were added thereto at 0° C., and the mixture was stirred at this temperature for 48 hours. The mixture was treated with a saturated sodium sulfite aqueous solution, and then extracted with ethyl acetate and dried over magnesium sulfate. The solvent was distilled off, and the residue was purified by silica gel column chromatography (20 g, eluted with hexane/ethyl acetate=2/1 (v/v) to obtain 190 mg (yield: 70%) of iodolactone of the formula (VI) as white crystals.
$^1$H-NMR (90 MHz, CDCl$_3$) δppm
1.92(1H, t), 2.2–3.0(4H, m), 3.61(2H, d),
3.8–4.3(2H, m), 4.50(2H, s), 5.00(1H, t),
7.1–7.6(5H, m)
MS; M+ =388, [M—OCH$_2$Ph]+ =281
m.p. 120°–121° C.
$[\alpha]_D^{25}$= −34.8° (c=1.041, CHCl$_3$)

The melting point and the specific rotation agreed substantially to the values m.p.: 120°–122° C. and $[\alpha]_D^{25}$= −34.0° (c)=1.1, CHCl$_3$) as disclosed in JACS 93 1491 (1971).

We claim:

1. A compound having the formula:

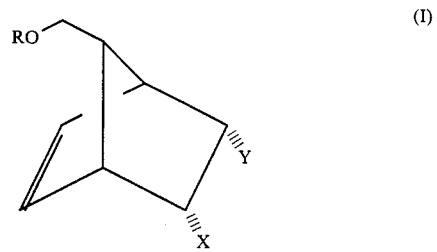

where R is a hydroxyl-protecting group and is a benzyl group which is unsubstituted or substituted on its benzene ring by one or two lower alkyl groups, bromine atoms or chlorine atoms, a lower alkoxy methyl group, or a lower alkylated silyl group, X is a hydrogen atom or a group of the formula:

formula:

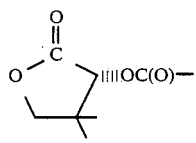

and when X is a hydrogen atom, Y is a group of the formula:

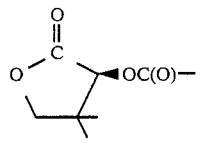

and when X is a group of the formula (i), Y is a hydrogen atom.

2. The compound according to claim 1, wherein Y is a hydrogen atom.

3. The compound according to claim 2, wherein R is a benzyl group which is unsubstituted or substituted on its benzene ring by one or two lower alkyl groups, bromine atoms or chlorine atoms.

4. The compound according to claim 1, wherein X is a hydrogen atom.

5. The compound according to claim 1, wherein Y is a hydrogen atom and R is a benzyl group.

* * * * *